United States Patent

Haertl

Patent Number: 5,537,860
Date of Patent: Jul. 23, 1996

[54] FLUID SENSOR INCLUDING SUBSTANTIALLY LINEAR FLOW RESISTOR

[75] Inventor: Hans-Georg Haertl, Karlsruhe, Germany

[73] Assignee: Hewlett-Packard Company, Palo Alto, Calif.

[21] Appl. No.: 288,766

[22] Filed: Aug. 11, 1994

[30] Foreign Application Priority Data

Feb. 24, 1994 [EP] European Pat. Off. ............. 94102766

[51] Int. Cl.$^6$ .................................................. G01N 11/00
[52] U.S. Cl. ..................... 73/54.14; 73/54.09; 73/861.59
[58] Field of Search ............................. 73/54.14, 54.09, 73/861.59

[56] References Cited

U.S. PATENT DOCUMENTS

| | | | |
|---|---|---|---|
| 1,863,090 | 6/1932 | Albersheim et al. | 73/54.09 |
| 2,589,251 | 3/1952 | Heinz | 73/54.09 |
| 2,700,891 | 2/1955 | Shafer | 73/54.09 |
| 2,960,861 | 11/1960 | Copland et al. | 73/54.09 |
| 2,962,891 | 12/1960 | Jansson | 73/54.09 |
| 2,988,914 | 6/1961 | Jones | 73/54.09 |
| 3,015,233 | 1/1962 | Ryder et al. | 73/861.59 |
| 3,024,642 | 3/1962 | Jones | 73/54.09 |
| 3,024,643 | 3/1962 | Jones | 73/54.09 |
| 3,102,423 | 9/1963 | Prindle | 73/861.59 |
| 3,198,009 | 8/1965 | Fishman et al. | 73/861.59 |
| 3,232,104 | 2/1966 | Fishman et al. | 73/861.59 |
| 3,232,105 | 2/1966 | Fishman et al. | 73/861.59 |
| 3,240,061 | 3/1966 | Bloom et al. | 73/861.59 |
| 3,263,494 | 8/1966 | Abbot | 73/54.09 |
| 3,266,309 | 8/1966 | Fishman et al. | 73/861.59 |
| 3,327,522 | 6/1967 | Hoyt | 73/54.09 |
| 3,338,097 | 8/1967 | Bloom et al. | 73/861.59 |
| 3,371,530 | 3/1968 | Howe | 73/861.59 |
| 3,559,464 | 2/1971 | Foust et al. | |
| 3,662,599 | 5/1972 | Masnik | 73/861.59 |
| 3,699,812 | 10/1972 | Masnik | 73/861.59 |
| 3,921,448 | 11/1975 | Masnik et al. | 73/861.59 |
| 4,496,287 | 1/1985 | Nelson et al. | 73/54.14 |
| 4,890,482 | 1/1990 | Maini | 73/54.14 |

FOREIGN PATENT DOCUMENTS

| | | | |
|---|---|---|---|
| 1295866 | 11/1962 | Germany | 76/861.59 |
| 2530474 | 8/1976 | Germany . | |
| WO85/02463 | 6/1985 | WIPO . | |

OTHER PUBLICATIONS

Thurston, G. B., "Viscoelasticity of Human Blood," *Biophysical Journal*, vol. 23, 1972, 1205–1216.
Simmonds data sheet.

*Primary Examiner*—Thomas P. Noland
*Assistant Examiner*—Jay L. Politzer

[57] ABSTRACT

The volumetric flow rate of a fluid is determined essentially independently of the properties of the fluid by guiding the volumetric fluid flow to be measured through an essentially linear flow resistor. An alternating flow of the fluid is superimposed on the volumetric fluid flow to be measured. Steady and alternating components of a pressure drop across the flow resistor are detected. A quantity representative of a property of the fluid is determined in response to the determined alternating component. The volumetric flow rate is calculated on the basis of the determined steady component and the quantity representing fluid property.

19 Claims, 4 Drawing Sheets

FLUID SENSOR INCLUDING SUBSTANTIALLY LINEAR FLOW RESISTOR

FIELD OF THE INVENTION

The present invention relates to a fluid sensor, a device for and method of determining the viscosity of a fluid, and a device for and method of determining the volumetric flow rate of a.

The present invention especially refers to sensors, measuring devices and measurement methods which operate according to the pressure measuring method and which depend, only to a minor extent, on the properties of the fluid to be measured, such as the viscosity thereof.

DESCRIPTION OF THE PRIOR ART

Fluid sensors for detecting a volumetric flow rate have been used for a considerable time in the field of chromatography. Various pressure measuring methods of measuring a volumetric flow rate are known.

One method uses impact pressure on a lug for measuring the volumetric flow rate. A lug projecting into the fluid flow is here deflected by the impact pressure of the fluid flowing past the lug. This deflection is a measure of the flow in question. This method is, however, fluid-dependent, its dynamic range is limited and it has a lower measuring limit which is very high.

Furthermore, the measurement depends on the position of the system and it is sensitive to vibrations. Another known pressure measuring method for determining the volumetric flow rate uses the impact pressure on a shutter or nozzle. The impact pressure at the shutter depends on the density of the fluid within the measurement range. This known method is also fluid-dependent, has a low dynamic range and is only suitable for high flow rates.

Still another known pressure measuring method involves measuring the differential pressure across an essentially linear flow resistor. This pressure measuring method makes use of a fluid sensor of the type shown in FIG. 6. The fluid sensor 600 shown in FIG. 6 comprises an essentially linear flow resistor 610, which is arranged in the fluid flow. A differential pressure sensor 620 is connected in parallel to said flow resistor 610, said differential pressure sensor being used for measuring the pressure difference across the flow resistor 610. The volumetric flow rate is then calculated on the basis of this measured pressure difference. This device only works if the properties of the fluid are known so a disadvantage of said approach is that it is also fluid-dependent.

SUMMARY OF THE INVENTION

Taking this prior art as a basis, it is the object of the present invention to provide a fluid sensor which does not require substantial a priori knowledge of the fluid to be measured.

In accordance with a first aspect of the invention, this object is achieved by a fluid sensor comprising: an essentially linear flow resistor which is arranged in a fluid flow; a differential pressure sensor which is arranged in parallel to the flow resistor and which produces a differential pressure signal; and a pump means which is arranged in parallel to the flow resistor and the differential pressure sensor and which is constructed such that it is capable of superimposing an alternating flow on the flow to be measured.

In a preferred embodiment of the invention, the differential pressure sensor is provided with a first diaphragm having an opening which extends through said first diaphragm at right angles to the main surfaces thereof, said first diaphragm being provided with first elements for measuring the diaphragm deflection.

In another preferred embodiment of the invention, the pump means is provided with second and third diaphragms and with first and second actuating members arranged on one side of the respective diaphragm, said actuating members being used for actively deflecting said second and third diaphragms and said second and third diaphragms being provided with second and third elements for measuring the diaphragm deflection. In a further preferred embodiment of the invention, the first, second and third elements for measuring the diaphragm deflection include one strain gauge or several strain gauges.

In a further preferred embodiment of the invention, the first and second actuating members are controlled so they move in opposite phase so the moving second and third diaphragms move in opposite directions.

In a further preferred embodiment of the invention, a first chamber is defined by the first and second diaphragms and a sensor housing; a second chamber is defined by the first and second diaphragms and the sensor housing; the first and the second chambers are interconnected via the flow resistor; a means is provided for supplying the fluid to be measured to the first chamber, and a means is provided for discharging the fluid to be measured from the second chamber.

In a further preferred embodiment of the invention, the sensor housing is provided with a flow passage for defining the flow resistor, said flow passage extending from the first chamber along one main side of the first diaphragm through the opening of said first diaphragm and along the other main side of said first diaphragm to the second chamber.

In a further preferred embodiment of the invention, the sensor housing has a structural design of such a nature that the free diaphragm surface of the second and third diaphragms is larger than that of the first diaphragm.

In a further preferred embodiment of the invention, the supply means includes an inlet capillary leading through a cover portion and the sensor housing into the first chamber; and the discharge means includes an outlet capillary leading through the sensor housing and the cover portion and then out of the second chamber.

In a further preferred embodiment of the invention, the first and second actuating members of the pump means have the following features: a first rear wall including of a thermally conductive material, said first rear wall being arranged on one lateral surface of the sensor housing and having a plurality of ribs; a second rear wall including of a thermally conductive material, said second rear wall being arranged on the other lateral surface of the sensor housing and having a plurality of ribs; a third chamber defined by the second diaphragm, the first rear wall and the sensor housing, said third chamber containing a liquid; a fourth chamber defined by the third diaphragm, the second rear wall and the sensor housing, said fourth chamber containing a liquid; and first and second Peltier elements for cyclically heating and cooling the liquids contained in the third and fourth chambers.

In a further preferred embodiment of the invention, the first and second actuating members of the pump means each include a piezoelectric actuating element.

In a further preferred embodiment of the invention, the first and second actuating members of the pump means each include a piston which is moved by magnetic fields.

In another preferred embodiment of the invention, the first and second actuating members of the pump means are provided with chambers which are acted upon by a pressure.

Another object of the present invention is to provide sensors, measuring devices and measurement methods which operate according to the pressure measuring method and which are adapted for measuring the fluid flow rate such that the measurement is independent from or only slightly influenced by the properties of the fluid to be measured, such as the viscosity thereof.

In accordance with a second aspect of the invention, this object is achieved by a device for determining the volumetric flow rate of a fluid, comprising: a fluid sensor having an essentially linear flow resistor which is arranged in a fluid flow; a differential pressure sensor which is arranged in parallel to the flow resistor and which produces a differential pressure signal; and a pump means which is arranged in parallel to the flow resistor and the differential pressure sensor and which is constructed such that it is capable of superimposing an alternating flow on the flow to be measured; and a volumetric flow rate determination means which derives a quantity representative of a fluid property from the alternating differential pressure signal which is generated by the differential pressure sensor and which is essentially proportional to the alternating flow, and which derives the volumetric flow rate from the steady component of the differential pressure signal generated by the differential pressure sensor as well as from the quantity representative of the fluid property.

In accordance with a third aspect of the invention, this object is achieved by a method of determining the volumetric flow rate of a fluid, comprising the steps of guiding the volumetric fluid flow to be measured through an essentially linear flow resistor; generating an alternating fluid flow and superimposing the same on the volumetric fluid flow to be measured; detecting the pressure drop across the flow resistor; determining the steady component and the alternating component of the pressure drop detected; determining a quantity representative of a fluid property of the fluid on the basis of the alternating component which has been determined; and calculating the volumetric flow rate on the basis of the steady component which has been determined as well as on the basis of the quantity representative of the fluid property.

Another object of the present invention is to provide a measuring device and a measurement method for determining the viscosity of a fluid.

In accordance with a fourth aspect of the invention, this object is achieved by a device for determining the viscosity of a fluid, comprising: a fluid sensor having an essentially linear flow resistor which is arranged in a fluid flow; a differential pressure sensor which is arranged in parallel to the flow resistor and which produces a differential pressure signal; and a pump means which is arranged in parallel to the flow resistor and the differential pressure sensor and which is constructed such that it is capable of superimposing an alternating flow on the flow to be measured; and a signal evaluation means determining a value representative of the viscosity on the basis of the alternating differential pressure signal which is generated by the differential pressure sensor and which is essentially proportional to the alternating flow.

In accordance with a fifth aspect of the invention, this object is achieved by determining the viscosity of a fluid, comprising the steps of arranging an essentially linear flow resistor in the fluid whose viscosity is to be determined; generating an alternating fluid flow through the flow resistor; detecting the alternating component of the pressure drop across the flow resistor; and determining the viscosity of the fluid on the basis of the detected alternating component.

BRIEF DESCRIPTION OF THE DRAWINGS

In the following, preferred embodiments of the present invention are described in detail with reference to the drawings enclosed, in which.

DESCRIPTION OF THE PREFERRED
EMBODIMENTS OF THE INVENTION

Prior to discussing a preferred embodiment of the fluid sensor according to the present invention, the measuring principle of the present invention is explained in detail with reference to FIG. 1 to 3.

Figure 1:
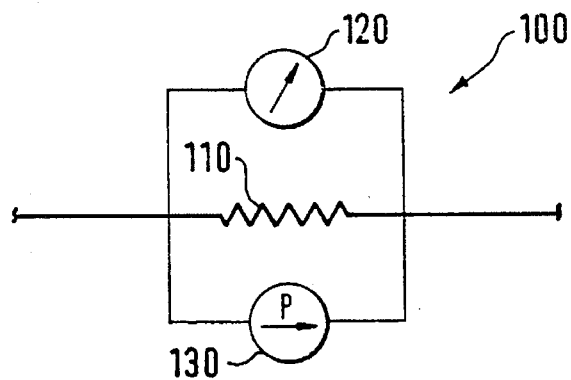
FIG. 1 is a schematic representation of the pressure sensor according to the present invention.

In FIG. 1 is shown a fluid sensor 100 according to broad principles of the present invention. Fluid sensor 100 includes an essentially linear flow resistor 110 which is arranged in a fluid flow to be measured. A differential pressure sensor 120, which produces a differential pressure signal, is connected in parallel to the flow resistor 110. A pump 130 superimposing an alternating flow on the flow to be measured is arranged in parallel to the flow resistor 110 and the differential pressure sensor 120. The amplitude of this alternating flow must be known to enable regular self-calibration of sensor 100.

Figure 2:
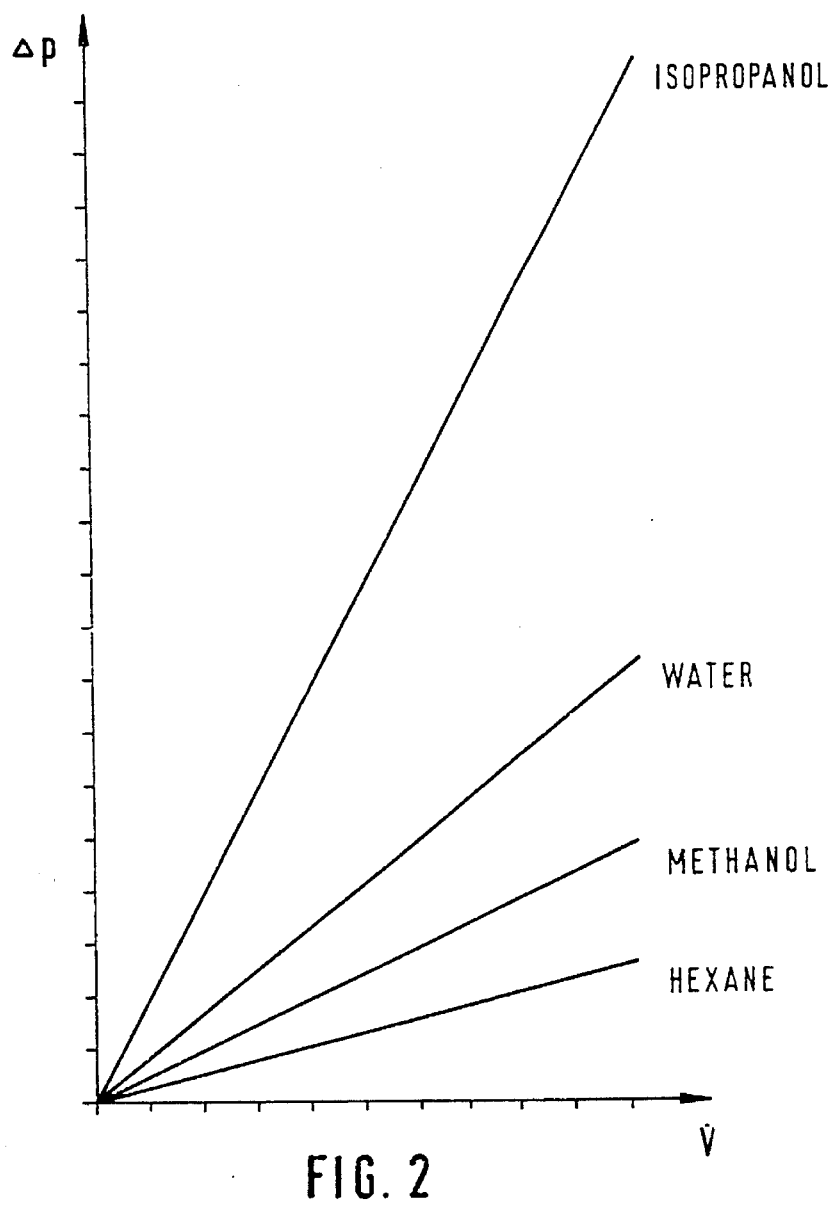
FIG. 2 is a graph which, on the basis of some examples, shows the dependence of the sensor signal on the viscosity of the fluid.

In FIG. 2 is shown the dependence of a sensor signal on the fluid viscosity on the basis of some examples, such as e.g. isopropanol, water, methanol or hexane. In practical operation, also arbitrary mixtures of fluids are used so that any ascending gradient between the characteristic curves shown is possible. Viscosities which are higher or lower than those shown in FIG. 2 are possible as well. Hence, the user will not be able to predict the viscosity of the fluid used. The pressure difference $\Delta p$ across the fluid resistor is calculated in accordance with the following equation:

$$\Delta p = V \times k \tag{1}$$

wherein k stands for a proportionality factor and V stands for the volumetric flow rate to be measured. Since the fluid viscosity is not known, the proportionality factor k mentioned in equation 1 is unknown.

Figure 3:
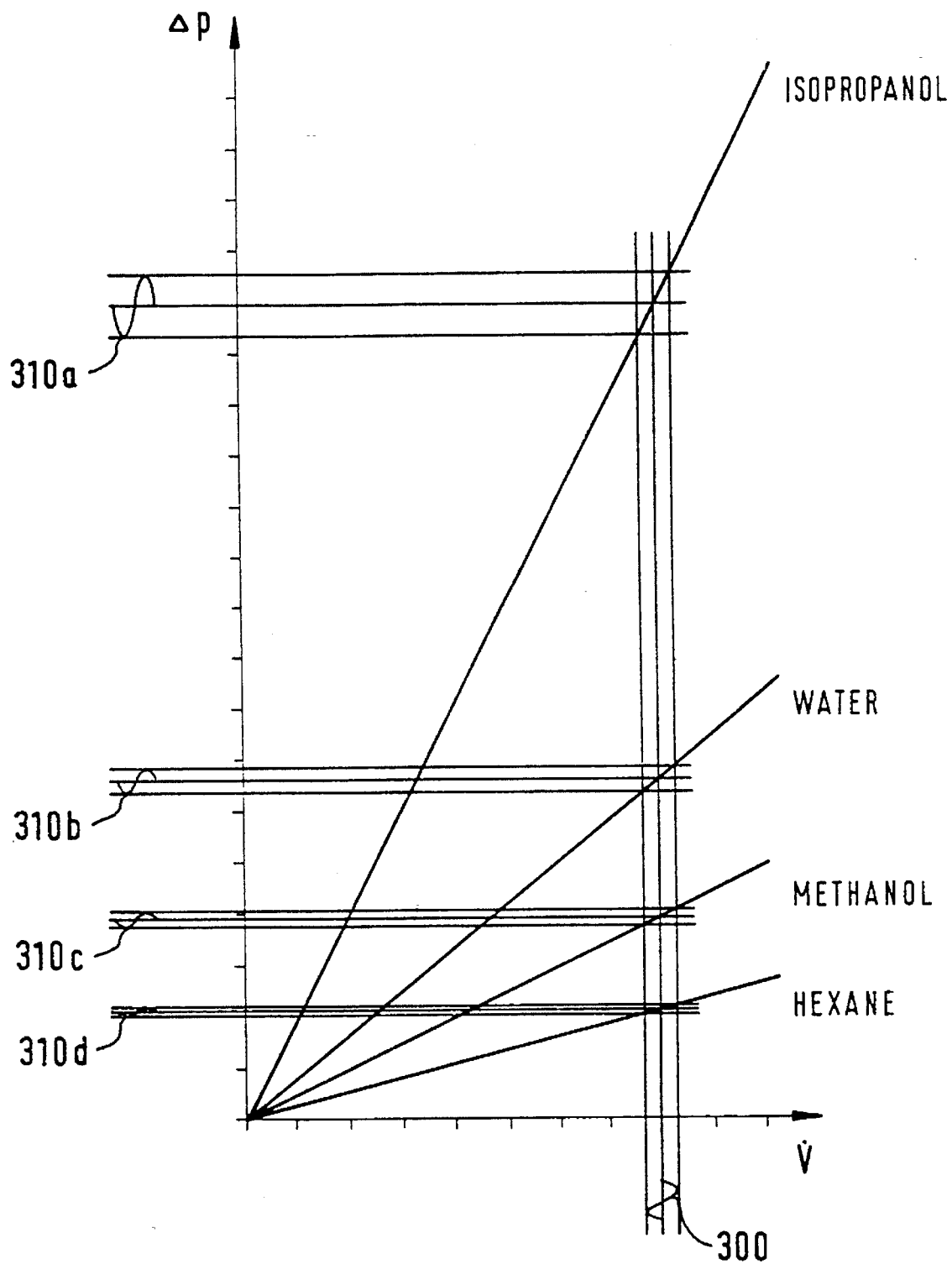
FIG. 3 is a graph which corresponds to the graph of FIG. 2 and which shows how a small introduced alternating flow is transformed into a pressure signal which is proportional to the fluid properties.

FIG. 3 shows the characteristic lines shown in FIG. 2, when an alternating flow 300 is superimposed on the volumetric flow rate V to be measured.

In view of the fact that the magnitude of the superimposed alternating flow 300 is known, the respective proportionality factor k for the fluid in question can be determined on the basis of the alternating flow representation 310a–310d in the differential pressure signal Δp. This is done without any previous knowledge of the fluid properties of the fluid.

In order to guarantee a precise measurement, the fluid sensor and the system must be decoupled to a sufficient degree. This decoupling can be effected e.g. by flow resistors located ahead of and behind the fluid sensor in the direction of flow.

Furthermore, the influence of the system on the fluid sensor must be ascertained and compensated for.

Insufficient coupling resistances in combination with large system capacities will otherwise have the effect that the superimposed alternating flow 300 will not flow through the flow resistor 110, but disappear fully or partly in the system.

A preferred embodiment of the present invention is described in detail with reference to FIG. 4.

As has already been described with reference to FIG. 1, the fluid sensor 100 according to the present invention comprises a flow resistor 110, a differential pressure sensor 120 connected in parallel to said flow resistor 110, and a pump 130 connected in parallel thereto.

Furthermore, the differential pressure sensor 120 comprises a first diaphragm 410 having a first opening 410a which extends through said diaphragm 410 at right angles to the main surfaces thereof. In addition, the first diaphragm 410 is provided with first elements which serve to measure the diaphragm deflection.

The pump 130 comprises second and third diaphragms 412, 414 and first and second actuating members. Said first and second actuating members are arranged on one side of the diaphragms 412, 414 and are used for actively deflecting the second and third diaphragms 412, 414. Just as the first diaphragm 410, the second and third diaphragms 412, 414 comprise second and third elements which serve to measure the deflection of the diaphragms 412, 414.

To the person skilled in the art it will be obvious that these first, second and third elements for measuring the diaphragm deflection may be provided with one or several strain gauges.

For producing the alternating flow 300 (FIG. 3) which is to be superimposed, the first and second actuating members for diaphrams 412, 414 are controlled so they are 180° phase shifted from each other to move the second and third diaphragms 412, 414 in opposite directions.

Figure 4:
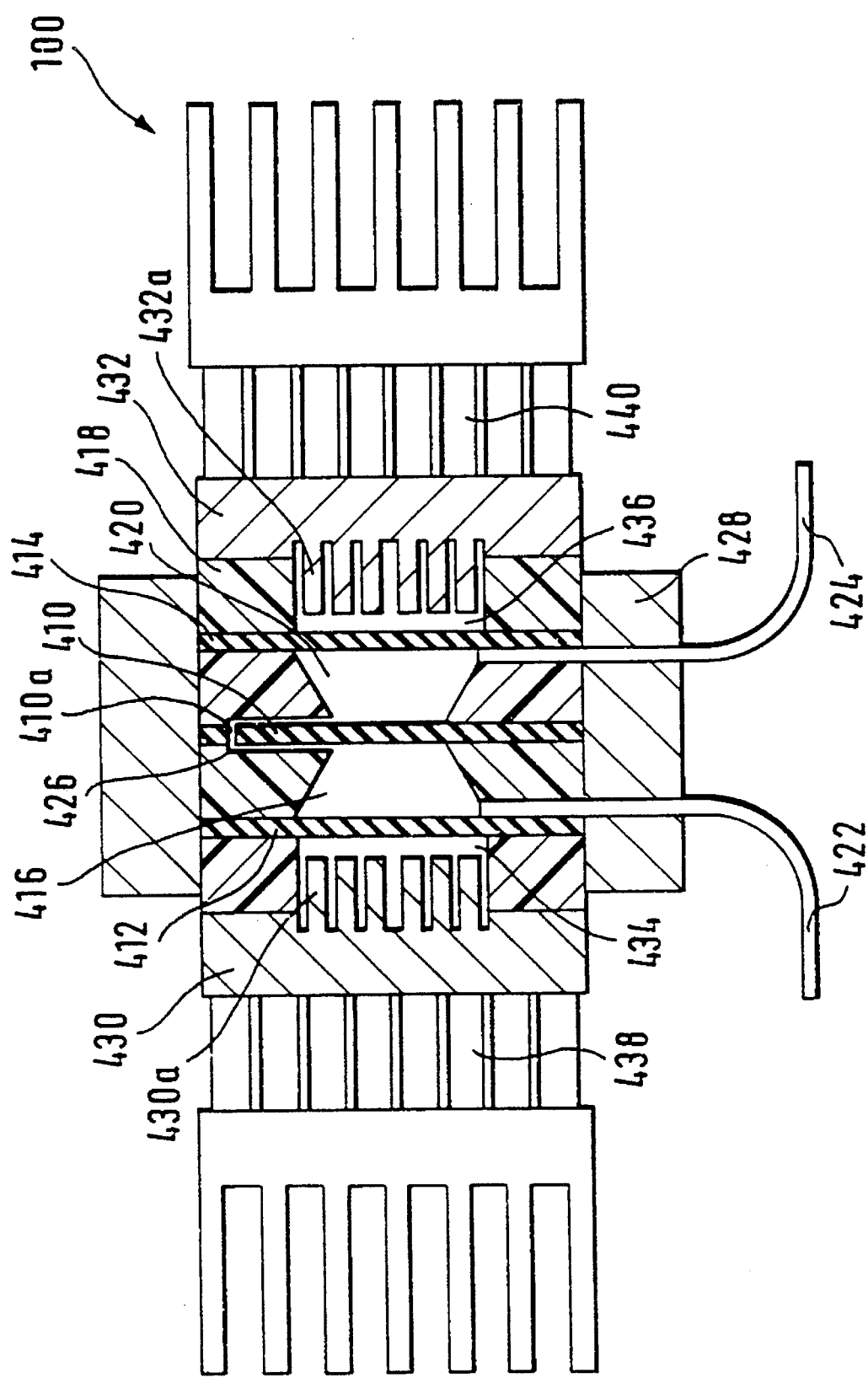
FIG. 4 is a sectional view of a fluid sensor according to the present invention.

As can be seen in FIG. 4, the fluid sensor 100 comprises a first chamber 416 defined by the first and second diaphragms 410, 412 and a sensor housing 418. A second chamber 420 is defined by the first and third diaphragms 410, 414 and the sensor housing 418. The first and second chambers 416, 420 are interconnected via linear flow resistor 110 including flow passage 426. The fluid sensor 100 is additionally provided with a conduit 422 for supplying the fluid to be measured to the first chamber 416 as well as with a conduit 424 for discharging the fluid to be measured from the second chamber 420.

In the embodiment of the fluid sensor 100 shown in FIG. 4, the sensor housing 418 is provided with the flow passage 426. This flow passage 426 extends from the first chamber 416 along one main side of the first diaphragm 410 through the opening 410a of the first diaphragm 410 and along the other main side of the first diaphragm 410 to the second chamber 420.

The sensor housing 418 has a structural design of such a nature that the free, i.e. easily deflected, diaphragm surface of the second and third diaphragms 412, 414 is larger area than that of the first diaphragm 410. In the preferred embodiment of the fluid sensor 100 according to the present invention, supply conduit 422 in a capillary extending through a cover portion 428 of the sensor housing 418 into the first chamber 416. Furthermore, discharge conduit 424 is a capillary extending through the sensor housing 418 and the cover portion 428 and then out of the second chamber 420.

In the preferred embodiment of the fluid sensor 100 according to the present invention, the first actuating member of the pump 130 has a first rear wall 430 including of a thermally conductive material. The first rear wall 430 is arranged on one lateral surface of the sensor housing 418 and has a plurality of ribs 430a. Furthermore, the second actuating member includes a second rear wall 432 including a thermally conductive material. The second rear wall 432 in arranged on the other lateral surface of the sensor housing 418 and has a plurality of ribs 432a. The second diaphragm 412, the first rear wall 430 and the sensor housing 418 define a third chamber 434. Furthermore, a fourth chamber 436 is defined by the third diaphragm 414, the second rear wall 432 and the sensor housing 418. The third and fourth chambers 434, 436 each contain a liquid. In order to achieve the desired pumping effect of the pump 130, the first and second actuating members each include a Peltier element 438, 440 for cyclically heating and cooling the liquid contained in the third and fourth chambers 434, 436.

To those skilled in the art it will be obvious that the first and second actuating members of the pump 130 may have different structural designs. The first and second actuating members may, for example, each comprise a piezoelectric actuating element or a piston which is moved by magnetic fields.

Furthermore, the first and second actuating members may be defined by chambers which are acted upon by a pressure.

Whereas the structural design and the mode of operation of the fluid sensor 100 according to the present invention have been described hereinbefore with reference to FIG. 4, various devices making use of the sensor according to the present invention will be described hereinbelow with reference to FIG. 5.

Figure 5:
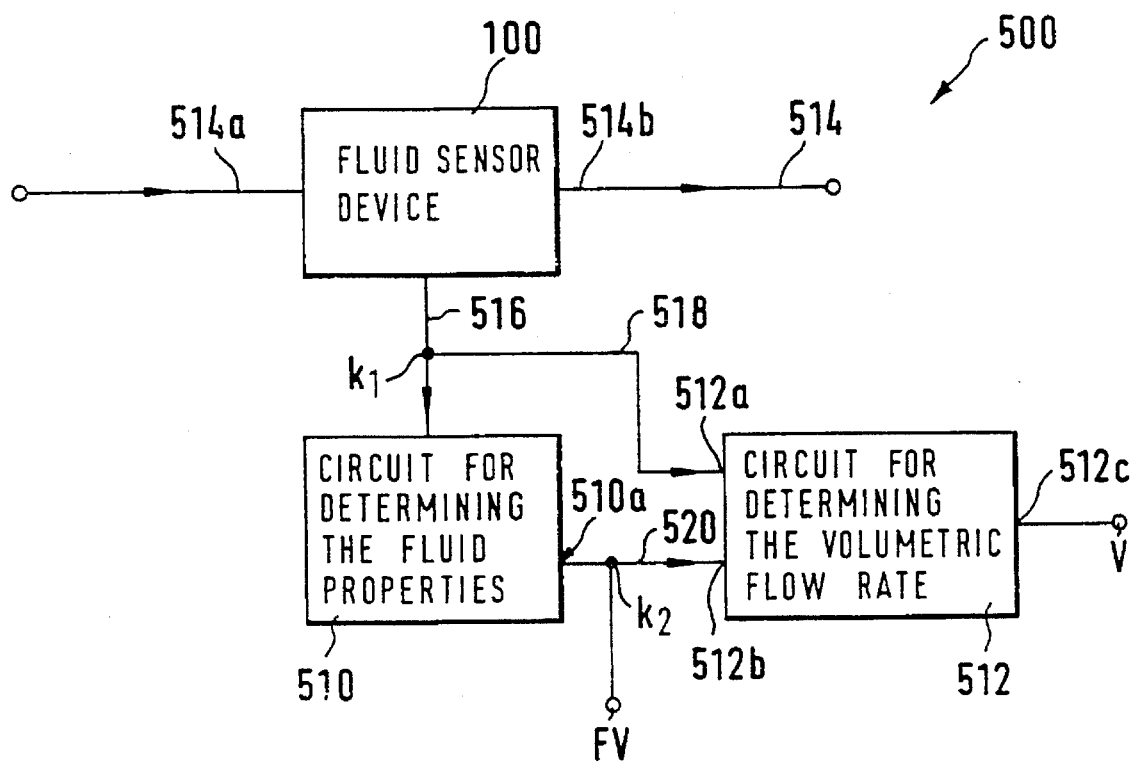
FIG. 5 is a block diagram of a device which uses the fluid sensor according to the present invention for determining the viscosity of a fluid and the volumetric flow rate of a fluid, respectively.
Figure 6:
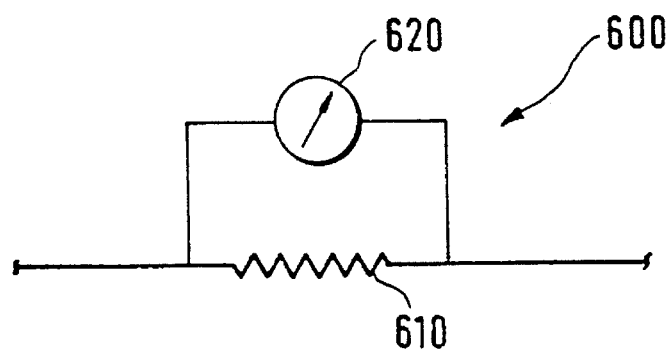
FIG. 6 is a diagram of a fluid sensor according to the prior art.

FIG. 5 is a block diagram with the fluid sensor 100, a circuit 510 for determining the fluid properties 512 and a circuit for determining the volumetric flow rate. The fluid sensor 100 is arranged in a fluid flow 514, the fluid entering the fluid sensor 100 on one side 514a thereof and leaving it on the other side 514b thereof.

The output signal of the sensor 100 is respectively supplied in parallel to circuit 510 via (1) a first input 512a of circuit 512 through signal line 516 and (2) node K1 and second signal line 518.

In the circuit 510 for determining the fluid properties, a value representative of the viscosity is determined by a signal evaluation means on the basis of the alternating differential pressure signal which is generated by the differential pressure sensor 120 and which is essentially proportional to the alternating flow 300. Through the output 510a of the circuit 510, this value is supplied via the third signal line 520 to a second input 512b of the circuit 512, whereupon it is tapped via the node K2 as output signal FV.

The circuit 512 determines the volumetric flow rate by deriving a quantity representative of a fluid property from the alternating differential pressure signal which is generated by the differential pressure sensor 120 and which is essentially proportional to the alternating flow. Circuit 512 also derives the volumetric flow rate V from the steady component of the differential pressure signal generated by the differential pressure sensor 120 as well as from the quantity FV which is representative of the fluid property. The value indicating the volumetric flow rate V is outputted via the output 512c of the circuit 512.

In summary, the liquids to be monitored have mass flow rate versus differential pressure variations across linear flow resistor 0, FIG. 1, as illustrated in FIGS. 2 and 3. From FIGS. 2 and 3 and equation (1), there is a linear relationship between the mass flow rate, v, and the differential pressure, Δp across resistor 110. The linear relationship is directly proportional to k, a function of the material having an unknown value that is indicative of the viscosity of the liquid flowing through gauge 100. In the present invention, the values of k, differential pressure (Δp) and mass flow rate (v) are determined.

The flow being monitored flows through linear resistor 110, in the form of diaphragm 410 and opening 410a, FIG. 4. The flow rate being monitored causes diaphragm 410 to deflect to an average value. The deflection of diaphragm 410 is modulated by activating diaphragms 412 and 414 so they move in opposite directions to change the velocity of the fluid acting on diaphragm 410. Diaphragms 412 and 414 are driven by oscillating the liquids in chambers 434 and 436, respectively coupled to Peltiet heat sources 438 and 440 by metal, high thermal conductivity walls 430 and 432. Hence diaphragm 410 oscillates about its average value.

The mass flow rate to be monitored is indicated in FIG. 3 by the vertical line centered on oscillation 300. The oscillating component of the mass flow rate caused by the movements of diaphragms 412, 414 is indicated in FIG. 3 by one cycle of oscillation 300. Oscillation 300 causes movement of diaphragm 410, as indicated above. Because of the linear relationship between mass flow rate and the pressure across diaphragm 410, the differential pressure across linear flow resistance 110, FIG. 1, is indicated for the different materials illustrated in FIG. 3 by the oscillatory waveforms 310a, 310b, 310c and 310d.

The amplitude of mass flow rate variation indicated by oscillation 300 is monitored since diaphragms 412 and 414 have position monitoring detectors, such as strain gauges or piezoelectric crystals, mounted thereon. From the incremental oscillation 300 imposed on the mass flow rate (Δv), as determined by the detectors on diaphragms 412 and 414, and the resulting oscillations of the differential pressure (Δ(Δp)), as detected by the movement of diaphragm 410, the slope (k) of the characteristic curves is determined. The slope k, indicative of the viscosity of the liquid flowing through gauge 100, is determined in accordance with the principles of differential calculus, as $$k = \frac{\Delta(\Delta p)}{\Delta v}.$$

The average deflection of diaphragm 410, as indicated by a DC component derived from the position detector on diaphragm 410, indicates the value of Δp in the graph of FIG. 3. Since the value of Δp and the value of k are known, the mass flow rate, (v), of the liquid flowing through gauge 100 is calculated from equation (1).

I claim:

1. A fluid sensor comprising:

an essentially linear flow resistor arranged in a fluid flow;

a differential pressure sensor arranged in parallel to the flow resistor and which produces a differential pressure signal (Δp); and a pump means arranged in parallel to the flow resistor and the differential pressure sensor for superimposing an alternating flow on the flow to be measured.

2. A fluid sensor according to claim 1, wherein the differential pressure sensor is provided with a first diaphragm having an opening which extends through said first diaphragm at right angles to main surfaces thereof, said first diaphragm being provided with first elements for measuring deflection of the diaphragm.

3. A fluid sensor according to claim 1, wherein the pump means is provided with second and third diaphragms and with first and second actuating members arranged on one side of the respective diaphragm, said actuating members being arranged for actively deflecting said second and third diaphragms, said second and third diaphragms including second and third elements for measuring deflection of the respective diaphragm.

4. A fluid sensor according to claim 3 wherein the first, second and third elements for measuring the diaphragm deflection include one or several strain gauges.

5. A fluid sensor according to claim 4, wherein the first and second actuating members are controlled with an 180° phase shift for achieving thus a movement of the second and third diaphragms in opposite directions.

6. A fluid sensor according to claim 3 wherein the first and second actuating members are controlled so they move the second and third diaphragms in opposite directions.

7. A fluid sensor according to claim 3 wherein a first chamber is defined by the first and second diaphragms and a sensor housing;

a second chamber is defined by the first and second diaphragms and the sensor housing;

the first and the second chambers are interconnected via the flow resistor;

a means is provided for supplying the fluid to be measured to the first chamber; and a means is provided for discharging the fluid to be measured from the second chamber.

8. A fluid sensor according to claim 7, wherein the sensor housing includes a flow passage for defining the flow resistor, said flow passage extending from the first chamber along one main side of the first diaphragm through the opening of said first diaphragm and along a second other main side of said first diaphragm to the second chamber.

9. A fluid sensor according to claim 7, wherein the sensor housing has a structural design so that a free diaphragm surface of the second and third diaphragms is larger than that of the first diaphragm.

10. A fluid sensor according to claim 7, wherein the supply means includes an inlet capillary leading through a cover portion and the sensor housing into the first chamber; and the discharge means includes an outlet capillary leading through the sensor housing and the cover portion and then out of the second chamber.

11. A fluid sensor according to claim 3, wherein the first and second actuating members of the pump means have the following feature:

a first rear wall including a thermally conductive material, said first rear wall being arranged on one lateral surface of the sensor housing and having a plurality of ribs;

a second rear wall including a thermally conductive material, said second rear wall being arranged on the other lateral surface of the sensor housing and having a plurality of ribs;

a third chamber defined by the second diaphragm, the first real wall and the sensor housing, said third chamber containing a liquid;

a fourth chamber defined by the third diaphragm, the second real wall and the sensor housing, said fourth chamber containing a liquid; and first and second Peltier elements for cyclically heating and cooling the liquids contained in the third and fourth chambers.

12. A fluid sensor according to claim 3, wherein the first and second actuating members of the pump means each include a piezoelectric actuating element.

13. A fluid sensor according to claim 3, wherein each of the first and second adjusting members of the pump means includes a piston which is moved by magnetic fields.

14. A fluid sensor according to claim 3, wherein the first and second actuating members of the pump means are provided with chambers which are acted upon by a pressure.

15. A fluid sensor according to claim 3, wherein the first, second, and third elements for measuring the diaphragm deflection include one or several strain gauges.

16. A device for determining the viscosity of a fluid, comprising:

a fluid sensor including:

an essentially linear flow resistor arranged in a fluid flow;

a differential pressure sensor arranged in parallel to the flow resistor for deriving a differential pressure signal; and a pump means arranged in parallel to the flow resistor and the differential pressure sensor and constructed so it is capable of superimposing an alternating flow on the flow to be measured;

and a signal evaluation means for determining a viscosity representative value on the basis of the alternating differential pressure signal generated by the differential pressure sensor and which is essentially proportional to the alternating flow.

17. A device for determining the volumetric flow rate of a fluid, comprising:

a fluid sensor including:

an essentially linear flow resistor arranged in a fluid flow;

a differential pressure sensor arranged in parallel to the flow resistor for producing a differential pressure signal;

a pump means arranged in parallel to the flow resistor and the differential pressure sensor for superimposing an alternating flow on the flow to be measured;

and a volumetric flow rate determination means for deriving a quantity representative of a fluid property from the alternating differential pressure signal which is generated by the differential pressure sensor and which is essentially proportional to the alternating flow, and which derives the volumetric flow rate from the steady component of the differential pressure signal generated by the differential pressure sensor as well as from the quantity representative of the fluid property.

18. A method of determining the volumetric flow rate of a fluid, comprising the steps of:

guiding the volumetric flow rate to be measured through an essentially linear flow resistor;

generating an alternating fluid flow and superimposing the same on the volumetric fluid flow to be measured;

detecting the pressure drop across the flow resistor;

determining the steady component and the alternating component of the detected pressure drop;

determining a quantity representative of a fluid property of the fluid on the basis of the determined alternating component; and calculating the volumetric flow rate on the basis of the determined steady component and on the basis of the quantity representative of the fluid property.

19. A method of determining the viscosity of a fluid, comprising the steps of:

inserting an essentially linear flow resistor in the fluid whose viscosity is to be determined;

imposing an alternating flow of the fluid in the flow resistor;

detecting the alternating component of the pressure drop across the flow resistor; and determining the viscosity of the fluid on the basis of the detected alternating component.

* * * * *